United States Patent [19]
Gabetta et al.

[11] Patent Number: 5,200,186
[45] Date of Patent: Apr. 6, 1993

[54] PROCESS FOR THE PREPARATION OF EXTRACTS HAVING HIGH CONTENT IN ANTHOCYANOSIDES

[75] Inventors: Bruno Gabetta; Gianfranco Zini, both of Milan, Italy

[73] Assignee: Inverni Della Beffa S.P.A., Milan, Italy

[21] Appl. No.: 562,216

[22] Filed: Aug. 3, 1990

[30] Foreign Application Priority Data

Aug. 11, 1989 [IT] Italy ................ 21515 A/89

[51] Int. Cl.$^5$ .............. A61K 35/78; A61K 31/35; C09B 61/00
[52] U.S. Cl. ................ 424/195.1; 8/646; 514/456
[58] Field of Search ............ 424/195.1; 8/646; 514/456

[56] References Cited

U.S. PATENT DOCUMENTS

| | | | |
|---|---|---|---|
| 4,211,577 | 7/1980 | Wallin | 106/288 |
| 4,258,055 | 3/1981 | Lietti | 424/283 |
| 4,376,781 | 3/1983 | Lietti | 424/283 |
| 4,413,004 | 11/1983 | Lietti | 424/283 |
| 4,857,327 | 8/1989 | Virdalm | 424/195.1 |
| 4,863,956 | 9/1989 | Gabetta | 514/453 |
| 4,925,871 | 5/1990 | Gabetta | 514/453 |

OTHER PUBLICATIONS

Steinmetz E. F. 1957 Codex Vegetabilis Amsterdam #972, #1016, #1178, #1206.
Martinelli E. M. Computer Aided Evaluation of . . . Anthocyanins, Analytica Chimica Acta 191 (1986) pp. 275-281.
Colantuoni A., Effects of *V. myrtillus* Anthocyanosides on Arterial Vasomotion, Drug Res. 41(11)9, 905-909 (1991).
"The Flavonoids", edited by J. B. Harborne, T. J. Mabry, Helga Mabry Chapman and Hall, London, p. 227.

*Primary Examiner*—Ronald W. Griffin
*Assistant Examiner*—Ralph Gitomer
*Attorney, Agent, or Firm*—Bucknam and Archer

[57] ABSTRACT

A process for the preparation of extracts with high content in anthocyanosides consists in treating plants, parts of plants or crude extracts with bisulfite ions to give anthocyanoside-bisulfite adducts. Said adducts are then eluted on non ionogenic resins at pH 5-6 and the obtained solution is extracted with polar organic solvents immiscible in water. The obtained extracts have a constant and standardized composition in anthocyanosides.

8 Claims, No Drawings

PROCESS FOR THE PREPARATION OF EXTRACTS HAVING HIGH CONTENT IN ANTHOCYANOSIDES

The present invention refers to a process for the preparation of extracts having high content in anthocyanosides, to the extracts obtainable from said process and the use thereof in the pharmaceutical and cosmetic industries.

The fruits of *Vaccinium myrtillus, Ribes nigrum, Vitis vinifera, Sambucus nigra* and other plants are the starting material used for the preparation of extracts used in therapy, namely in the pathology of capillaries and in ophthalmology.

The pharmacological activity of said extracts is *V.myrtillus* fruits, for instance, the 3-O-glucosides, the 3-O-galactosides and the 3-O-arabinosides of the aglycones cyanidin, delphinidin, petunidin, peonidin and malvidin, are present in well-defined ratios.

Their content in extracts may be evaluated by gas-chromatographic analysis or by HPLC (J. Chromat., 279, 365, 1983). Using these specific analytical methods, it is found that the content in anthocyanosides in the commercially available *V. myrtillus* extracts range from 2% to 40%.

Besides anthocyanosides, mineral salts, common organic acids such as citric or tartaric acid, carbohydrates, flavonic glycosides and cathechic substances with different polymerization degree are present.

It is known that the percent anthocyanosides content in *V.myrtillus* and *V.vinifera* extracts may be increased by purification processes: purifications with solvents (FR-A-2456747), treatment with different kinds of resins (FR-A-2299385; FR-A-2378070; DE 3310340) and inverted osmosis (FR-A-2358313) are claimed. All these processes must be carried out in controlled conditions of temperature and acidity, since the anthocyanosides are easily subjected to degradation phenomena of hydrolytic or oxidative kind, the latter especially at pH values higher than 3.

While the known processes allow the elimination of inorganic salts, organic acids and carbohydrates, the purification from flavonic glycosides and from cathechic tannins, having polarity and solubility very close to those of anthocyanosides, is not easy. It follows for instance that standardized *V.myrtillus* extracts with high and specific anthocyanosides content have not been up to now prepared.

The present invention concerns a process allowing the preparation of a standardized extract containing the glycosides of cyanidin, delphinidin, peonidin and malvidin at high titer and in the natural ratios, starting from low titer extracts or from the fruits.

Accordingly, a commercial low titer *V.myrtillus* fruits extract is added to an aqueous solution containing an excess of bisulfite ions, with whom it is known that the anthocyanosides form adducts (J. B. Harborne, The Flavonoids, Chapman and Hall Ed. London, p. 227). The bisulfite ions may be prepared by usual methods, for example by addition of sulfur dioxide or simply by addition of sodium methabisulfite.

The starting *V.myrtillus* extract, containing from 2% to 40% of anthocyanosides, is stirred for some hours, preferably 2-4 hours, with 20-30 volumes of aqueous solution containing at least 5 moles of bisulfite ions per mole of anthocyanoside.

The solution of bisulfite adducts, whose pH is generally ranging from 1 to 3.5, is then alkalinized till pH ranging from 5 to 6 and then eluted through a column containing a non-ionogenic polymeric resin. While in acidic conditions the anthocyanosides-bisulfite adducts are absorbed on the resin together with other phenolic substances, at pH 5-6 the bisulfite adducts remain surprisingly dissolved in the aqueous phase together with the salts, the organic acids and the carbohydrates and they may be separated from the polyphenolic components present in the starting extract which are absorbed in the column.

The resins which may be used for this purification are non-ionogenic cross-linked resins, obtained by polymerization of styrene, divinylbenzene, trivinylbenzene, alkylvinylbenzene, acrylvinylbenzene and the like. The amount of resin to be used increases according to the increase of the amount of phenolic substances to be absorbed. Generally, about 1 l of resin is needed to absorb 10 grams of glycosylflavones and cathechic tannins. These substances may be then recovered by washing the resin with an organic solvent such as acetone or methanol.

The aqueous solution eluted from the resin containing the bisulfite adducts together with inorganic salts, organic acids and carbohydrates, is concentrated under vacuum till a volume of 10-20 times the solid residue and acidified to pH 1-2 by addition of an acid, e.g. diluted hydrochloric acid. The cleavage of the bisulfite-anthocyanosides adducts is completed by means of a stream of inert gas such as nitrogen, removing sulfur dioxide. The gas flow is bubbled in a sodium hydroxide aqueous solution so as to avoid sulfur dioxide pollution in the environment.

The anthocyanosides are then separated from the other components by extraction with a polar organic solvent immiscible with water, e.g. butanol or amyl alcohols, extracting the anthocyanosides in chloride form.

After concentrating the organic phase under vacuum, the extract with high content in anthocyanosides may be isolated by lyophilization, atomization or preferably by precipitation with an aprotic solvent, e.g. ethyl acetate.

The titer in anthocyanosides in the obtained *V.myrtillus* extracts is $\geq$ 90% according to HPLC analysis, using cyanidin 3-O-glucoside as reference.

Similarly, anthocyanoside extracts may be obtained from other fruits, e.g. from *Ribes nigrum* with titers=80%.

Besides the high titer in anthocyanosides, the described process allows to obtain an extract practically free from hydrolytic degradation products (anthocyanidins). This is an important aspect in the preparation of standardized active principle for the pharmaceutical use.

A further advantage of the described process consists of the possibility of preparing extracts in which the natural ratio of the *V.myrtillus* anthocyanosides as reported in Anal. Chim. Acta, 191, 275, 1986, is mantained.

The extracts obtainable from the above process are useful in the pharmaceutical and cosmetic industries where they can be used, according to usual methods, as active principles of pharmaceutical and cosmetic compositions, whose indications are identical to those of the presently known similar compositions.

EXAMPLE 1

Preparation of an Extract with High Titer in Anthocyanosides from V.myrtillus fruits Freezed fruits of V.myrtillus fruits (1.46 Kg.), containing 6.4 g of anthocyanosides, are extracted with 5×1 l of 50% aqueous methanol, each extraction carried out for 4 hours. The extract is concentrated under vacuum until a volume of 2.6 l, the solution is added with 5.5 g of sodium bisulfite and stirred for 3 hours at room temperature. The mixture is neutralized to pH 5.5 by addition of a 10% sodium hydroxide solution and charged on a column containing 1.5 l of a non-polar polystyrenic resin, having a particle size of 20–50 mesh and a surface area of 750 m$^2$/g. The column is washed with 8 l of purified water eluting at a flowrate of 1.5 l.

The aqueous percolates are concentrated under vacuum up to a volume of 2 l and acidified to pH 1 by addition of concentrated hydrochloric acid. Nitrogen is bubbled into the solution, collecting the released sulfur dioxide in an alkaline solution. The aqueous solution is then extracted with 6×500 ml of n-butanol. The collected organic phases are concentrated under vacuum till a volume of 500 ml, washed with 100 ml of a 1% HCl solution and concentrated under vacuum up to a volume of about 50 ml. The concentrated butanol solution is then poured under stirring into 700 ml of ethyl acetate. After standing overnight, the precipitated solid is filtered and dried under vacuum at 40° C.

7.1 g of an extract having HPLC titer of 90.2% are obtained. The percent composition of anthocyanosides is the following: delphinidin galactoside 13.20, delphinidin glucoside 15.00, delphinidin arabinoside 9.06, cyanidin galactoside 7.25, cyanidin glucoside 9.06, cyanidin arabinoside 4.41, petunidin galactoside 3.88, petunidin glucoside 9.07, petunidin arabinoside 1.94, peonidin galactoside 0.65, peonidin glucoside 3.45, peonidin arabinoside 0.24, malvidin galactoside 3.02, malvidin glucoside 9.06, malvidin arabinoside 0.95%.

EXAMPLE 2

Preparation of an Extract with High Titer of Anthocyanosides from a Commercial V.myrtillus Extract 30 g of commercial V.myrtillus extract (titer in anthocyanosides 35%) are dissolved in 1 l of aqueous solution containing 8 g of sodium bisulfite and the obtained solution is stirred at room temperature for 3 hours. A 10% sodium hydroxide solution is added till pH 5.2 and the solution is eluted through a column containing 2.5 l of a non-polar polystyrenic resin, having a particular size of 20–50 mesh and a surface area of 750 m$^2$/g, at a flow-rate of 2 l/h. The column is then washed with 8 l of demineralized water and the eluted aqueous solution is concentrated under vacuum up to a volume of 1 liter and acidified to pH 1 by concentrated hydrochloric acid, removing sulfur dioxide by bubbling nitrogen therein.

The aqueous solution is extracted with 5×500 ml of n-butanol and the organic extracts are collected, concentrated up to 50 ml and poured under stirring into 1 l of ethyl acetate. After standing overnight, the precipitated solid is filtered and dried under vacuum at 40° C. 8.7 g of an extract with a titer in anthocyanosides of 92% (HPLC) are obtained.

The percent composition is substantially similar to that of example 1.

EXAMPLE 3

Preparation of an Extract with High Titer in Anthocyanosides from a Commercial R.nigrum Extract 30 g of a commercial R.nigrum extract (titer 22.5% in anthocyanosides having the following composition: delphinidin glucoside 3.6, delphinidin rutinoside 9.6, cyanidin glucoside 1.4, cyanidin rutinoside 7.9) are dissolved in 1 l of an aqueous solution containing 6 g of sodium bisulfite and washed as described in example 2.

8 g of an extract with titer in anthocyanosides of 80% are obtained.

We claim:

1. A process for the preparation of an extract having high content of anthocyanosides which consists of:
   (a) reacting for 2–4 hours at room temperature an extract of fruits of Vaccinium muyrtillus, Ribes nigrum, Vitis vinifera or Sambucus nigra, containing 2–40% of anthocyanosides in addition to organic acids, salts, carbohydrates, flavonic glycosides, polyphenolic compounds and catechic tannins with 20–30 volumes of an aqueous solution containing at least 5 moles of bisulfite ion per mole of anthocyanosides to form a solution of an anthocyanoside-bisulfite adduct of pH 1–3.5;
   (b) adjusting the pH of said solution from step a) to 5–6 by addition of 10% aqueous alkali and passing said solution through a column containing a resin obtained by polymerization of styrene, the amount of said resin being about 1 liter of resin per 10 grams of said flavonic glycosides and said catechic tannins to be absorbed, whereby said bisulfite adduct is eluted in the aqueous solution together with said salts, said organic acids and said carbohydrates while said polyphenolic compounds and said catechic tannins remain absorbed on said column;
   (c) acidifying to pH 1–2 said aqueous solution from step b) by addition of hydrochloric acid whereby the anthocyanoside-bisulfite adduct is cleaved, completing the cleavage by passing a stream of an inert gas in said aqueous solution, and extracting said aqueous solution with butanol or amyl alcohol whereby said anthocyanosides are obtained in a butanol or amyl alcohol solution, concentrating said butanol or amyl alcohol solution and recovering said extract of anthocyanosides therefrom.

2. The process according to claim 1 wherein said extract of anthocyanosides is recovered from said butanol or amyl alcohol solution after concentration by lyophilization.

3. The process according to claim 1 wherein said extract of anthocyanosides is recovered from said butanol or amyl alcohol solution after concentration by atomization.

4. The process according to claim 1 wherein ethyl acetate is added to the butanol or amyl alcohol solution after concentration to precipitate said extract having a high content of anthocyanosides.

5. The process according to claim 1 wherein said extract of fruit in step a) contains the glycosides of a member selected from the group consisting of cyanidine, delphinidine, petunidine, peonidine, malvidine and mixtures thereof.

6. The process according to claim 1 wherein said extract of fruit in step a) is prepared from 1.46 kg of frozen V.myrtillus fruits containing 6.4 g of anthocyanosides by extraction with 1 liter of 50% aqueous methanol, five times, each extraction being carried out for four hours, and concentrating the extract to a volume of 2.6 liters.

7. The extract obtained by the process according to claim 1 wherein an extract of *V.myrtillus* fruits is used in step a), and which contains said anthocyanosides in an amount greater or equal to 90%.

8. The extract obtained by the process according to claim 6 wherein said anthocyanoside content is 90.2%.

* * * * *